(12) United States Patent
Arnaud et al.

(10) Patent No.: US 7,993,661 B2
(45) Date of Patent: Aug. 9, 2011

(54) SKIN MAKE-UP COMPOSITION COMPRISING A RESIN

(75) Inventors: Pascal Arnaud, L'Hay les Roses (FR); Shaoxiang Lu, Plainsboro, NJ (US)

(73) Assignee: L'Oreal, Paris (FR)

( * ) Notice: Subject to any disclaimer, the term of this patent is extended or adjusted under 35 U.S.C. 154(b) by 1011 days.

(21) Appl. No.: 11/484,625

(22) Filed: Jul. 12, 2006

(65) Prior Publication Data
US 2007/0014745 A1    Jan. 18, 2007

Related U.S. Application Data

(60) Provisional application No. 60/698,884, filed on Jul. 13, 2005.

(51) Int. Cl.
*A61K 8/00* (2006.01)
*A61K 8/92* (2006.01)

(52) U.S. Cl. .................. 424/400; 523/102; 523/105

(58) Field of Classification Search .................. None
See application file for complete search history.

(56) References Cited

U.S. PATENT DOCUMENTS

| | | | | |
|---|---|---|---|---|
| 4,536,405 A * | 8/1985 | Nara et al. | | 514/781 |
| 4,918,130 A * | 4/1990 | Kano et al. | | 524/499 |
| 5,618,883 A * | 4/1997 | Plamthottam et al. | | 525/98 |
| 5,961,998 A | 10/1999 | Arnaud et al. | | |
| 6,132,665 A * | 10/2000 | Bui et al. | | 264/308 |
| 6,187,300 B1 * | 2/2001 | Motley et al. | | 424/65 |
| 6,517,818 B1 * | 2/2003 | Golz-Berner et al. | | 424/64 |
| 6,524,594 B1 * | 2/2003 | Santora et al. | | 424/401 |
| 6,544,642 B2 * | 4/2003 | Cinelli et al. | | 428/343 |
| 2002/0168335 A1 * | 11/2002 | Collin | | 424/78.35 |

FOREIGN PATENT DOCUMENTS

WO    WO 02/41854    * 5/2002

OTHER PUBLICATIONS

U.S. Appl. No. 09/492,796, filed Jan. 28, 2000, Arnaud, et al.
U.S. Appl. No. 08/815,577, filed Mar. 12, 1997, Arnaud, et al.

* cited by examiner

*Primary Examiner* — Andrew D Kosar
*Assistant Examiner* — Lori K Mattison
(74) *Attorney, Agent, or Firm* — Oblon, Spivak, McClelland, Maier & Neustadt, L.L.P.

(57) ABSTRACT

The present invention relates to a skin make-up or care composition containing a liquid fatty phase having at least one resin having a number-average molecular weight of less than or equal to 10 000 g/mol, chosen from rosin, rosin derivatives, hydrocarbon-based resins, and mixtures thereof. The invention also relates to a non-therapeutic use of the invention composition in a process for making up or caring for the skin and for obtaining a deposit on the skin which has good transfer resistance, in particular in the presence of sebum.

16 Claims, No Drawings

SKIN MAKE-UP COMPOSITION COMPRISING A RESIN

REFERENCE TO PRIOR APPLICATIONS

This application claims priority to U.S. provisional application 60/698,884 filed Jul. 13, 2005, incorporated herein by reference.

FIELD OF THE INVENTION

The present invention relates to a skin make-up or care composition comprising a liquid fatty phase and at least one low molecular weight resin.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Cosmetic make-up compositions such as foundations, body make-up products, concealer products, eyeshadows or powders, generally comprise fatty substances such as oils and/or waxes, and a particulate phase generally composed of fillers and of pigments. They can thus be in the form of an anhydrous gel, in the form of a stick or rod or in the form of a supple paste. They can also be in the form of a powder, which can, for example, be loose, compacted or pressed. The make-up compositions can also comprise water or a hydrophilic phase, and then in particular be in the form of an oil-in-water emulsion, water-in-oil emulsion or multiple emulsion, in particular when it is a foundation or a tinted cream.

The care compositions can in particular be sun compositions or deodorants.

Foundation compositions are commonly used to give the skin, in particular the face, an aesthetic colour. These make-up products generally contain oils, pigments and/or fillers and, optionally, additives such as cosmetic or dermatological active agents.

These compositions, when they are applied to the skin, have the drawback of transferring, i.e. of becoming at least partly deposited, leaving traces, on certain supports with which they come into contact, and in particular a piece of clothing or the skin. A mediocre staying power of the film applied ensues, making it necessary to regularly renew the application of the composition. Moreover, the appearance of these unacceptable traces, in particular on shirt collars, can dissuade certain women from using this type of make-up.

Furthermore, the sebum excreted by the skin over time also modifies the properties of the make-up. In particular, the sebum does not promote adhesion of the make-up to the skin and the transfer of the make-up is even greater, engendering a notable loss of the make-up remaining on the skin.

"Transfer-free" skin make-up compositions which have the advantage of forming a transfer-resistant deposit, in particular in the presence of sebum, especially which does not become deposited, at least in part, on the supports with which they come into contact (clothing, fabrics), are therefore sought.

OBJECTS OF THE INVENTION

One object of the present invention is to provide a novel way of formulating a cosmetic product which makes it possible to obtain good transfer-resistance properties, in particular in the presence of sebum.

SUMMARY OF THE INVENTION

Now, the Applicant has found, surprisingly, that, by introducing, into a cosmetic skin make-up or care composition, a specific resin and at least one oil, it is possible to produce a make-up product that exhibits very good staying power.

DETAILED DESCRIPTION OF THE PREFERRED EMBODIMENTS

A subject of the present invention is a skin make-up or care composition comprising a liquid fatty phase comprising at least one resin having a number-average molecular weight of less than or equal to 10 000 g/mol, chosen from rosin, rosin derivatives, hydrocarbon-based resins, and mixtures thereof.

Advantageously, the composition is capable of forming a deposit having a transfer index in the presence of sebum of less than or equal to 3.

A subject of the invention is also a non-therapeutic skin make-up or care process comprising the application to the skin of a composition as defined above.

A subject of the invention is also the use of a composition as defined above, for obtaining a deposit, in particular a make-up, on the skin which has good transfer resistance, in the presence of sebum.

Resin

The resin used in the composition according to the invention preferably has a number-average molecular weight of less than or equal to 10 000 g/mol, in particular ranging from 250 to 10 000 g/mol, preferably less than or equal to 5000 g/mol, in particular ranging from 250 to 5000 g/mol, better still less than or equal to 2000 g/mol, in particular ranging from 250 to 2000 g/mol, and even better still less than or equal to 1000 g/mol, in particular ranging from 250 to 1000 g/mol.

The number-average molecular weight (Mn) are determined by gel permeation liquid chromatography (THF solvent, calibration curve established with linear polystyrene standards, refractometric detector).

The resin of the composition according to the invention is advantageously a "tackifying" resin. Such resins are in particular described in the Handbook of Pressure Sensitive Adhesive, edited by Donatas Satas, $3^{rd}$ edition, 1989, pp. 609-619.

The resin of the composition according to the invention is chosen from rosin, rosin derivatives, hydrocarbon-based resins, and mixtures thereof.

The rosin is a mixture comprising predominantly organic acids known as rosin acids (mainly acids of abietic type and of pimaric type).

Three types of rosin exist: the rosin ("gum rosin") obtained by incision on live trees, wood rosin, which is extracted from pine wood or stumps, and tall oil ("tall oil rosin") which is obtained from a by-product originating from the production of paper.

The rosin derivatives may be derived in particular from the polymerization, hydrogenation and/or esterification (for example with polyhydric alcohols such as ethylene glycol, glycerol or pentaerythritol) of rosin acids. Mention may, for example, be made of the rosin esters sold under the reference Foral 85, Pentalyn H and Staybelite Ester 10 by the company Hercules; Sylvatac 95 and Zonester 85 by the company Arizona Chemical, or Unirez 3013 by the company Union Camp.

The hydrocarbon-based resins are chosen from low molecular weight polymers which can be classified, according to the type of monomer that they comprise, as:

indene hydrocarbon-based resins such as the resins derived from the polymerization of a predominant proportion of indene monomer and a minor proportion of monomer chosen from styrene, methylindene, methylstyrene, and mixtures thereof. The resins can optionally be hydrogenated. These resins can have a molecular weight ranging from 290 to 1150 g/mol.

As examples of indene resins, mention may be made of those sold under the reference Escorez 7105 by the company Exxon Chem., Nevchem 100 and Nevex 100 by the company Neville Chem., Norsolene S105 by the company Sartomer, Picco 6100 by the company Hercules, and Resinall by the company Resinall Corp., or the hydrogenated indene/methylstyrene/styrene copolymers sold under the name "Regalite" by the company Eastman Chemical, in particular Regalite R 1100, Regalite R 1090, Regalite R7100, Regalite R1010 Hydrocarbon Resin and Regalite R1125 Hydrocarbon Resin;

aliphatic pentanediene resins such as those derived from the polymerization predominantly of the 1,3-pentanediene (trans or cis-piperylene) monomer and of a minor monomer chosen from isoprene, butene, 2-methyl-2-butene, pentene and 1,4-pentanediene, and mixtures thereof. These resins may have a molecular weight ranging from 1000 to 2500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of a first monomer chosen from indene and styrene, and of a second monomer chosen from cyclopentanediene dimers such as dicyclopentanediene, methyldicyclopentanediene or other dimers of pentanediene, and mixtures thereof. These resins generally have a molecular weight ranging from 500 to 800 g/mol, such as, for example, those sold under the reference Betaprene BR100 by the company Arizona Chemical Co., Neville LX-685-125 and Neville LX-1000, by the company Neville Chem., Piccodiene 2215 by the company Hercules, Petro-Rez 200 by the company Lawter or Resinall 760 by the company Resinall Corp.;

diene resins of isoprene dimers such as the terpenic resins derived from the polymerization of at least one monomer chosen from α-pinene, β-pinene, limonene, and mixtures thereof. These resins may have a molecular weight ranging from 300 to 2000 g/mol. Such resins are sold, for example, under the name Piccolyte A115 and S125 by the company Hercules, and Zonorez 7100 or Zonatac 105 Lite by the company Arizona Chem.

Mention may also be made of certain modified resins, for instance the hydrogenated resins such as those sold under the name Eastotac C6-C20 Polyolefin by the company Eastman Chemical Co., under the reference Escorez 5300 by the company Exxon Chemicals, or else the Nevillac Hard or Nevroz resins proposed by the company Neville Chem., the Piccofyn A-100, Piccotex 100 or Piccovar AP25 resins proposed by the company Hercules, or the SP-553 resin proposed by the company Schenectady Chemical Co.

According to a preferred embodiment, the resin is chosen from indene-hydrocarbon-based resins, in particular the hydrogenated indene/methylstyrene-styrene copolymers sold under the name "Regalite" by the company Eastman Chemical, such as Regalite R 1100, Regalite R 1090, Regalite R7100, Regalite R1010 Hydrocarbon Resin, and Regalite R1125 Hydrocarbon Resin.

The resin may be present in the composition according to the invention in any amount, preferably at a content ranging from 0.1% to 30% by weight, relative to the total weight of the composition, more preferably ranging from 0.3% to 15% by weight, even more preferentially ranging from 0.5% to 10% by weight.

Fatty Phase

The composition according to the invention comprises a liquid fatty phase.

The liquid fatty phase preferably comprises at least one oil chosen from volatile oils, non-volatile oils, and mixtures thereof.

According to a preferred embodiment, the composition according to the invention comprises at least one volatile oil.

For the purpose of the invention, the term "volatile oil" is intended to mean any oil capable of evaporating on contact with the skin, at ambient temperature and atmospheric pressure. The volatile oils of the invention are volatile cosmetic oils which are liquid at ambient temperature and which have a non-zero vapour pressure, at ambient temperature and atmospheric pressure, ranging in particular from 0.13 Pa to 40 000 Pa (0.001 to 300 mm Hg), and preferably ranging from 1.3 to 1300 Pa (0.01 to 10 mm Hg).

The volatile oil can be chosen from hydrocarbon-based volatile oils, silicone volatile oils, fluorinated volatile oils, and mixtures thereof.

According to a preferred embodiment, the composition according to the invention comprises at least one hydrocarbon-based volatile oil.

The term "hydrocarbon-based oil" is intended to mean an oil containing mainly hydrogen and carbon atoms, and optionally oxygen, nitrogen, sulphur and/or phosphorus atoms.

The volatile hydrocarbon-based oils can be chosen from hydrocarbon-based oils having from 8 to 16 carbon atoms, and in particular $C_8$-$C_{16}$ branched alkanes such as $C_8$-$C_{16}$ isoalkanes of petroleum origin (also called isoparaffins), for instance isododecane (also called 2,2,4,4,6-pentamethylheptane), isodecane or isohexadecane, and, for example, the oils sold under the trade names Isopar® or Permethyl®.

As volatile oils, use may also be made of volatile silicones, for instance volatile linear or cyclic silicone oils, in particular those having a viscosity $\leq 5$ centistokes ($5 \times 10^{-6}$ $m^2/s$), and having in particular from 2 to 10 silicon atoms, preferably from 2 to 7 silicon atoms, these silicones optionally comprising alkyl or alkoxy groups having from 1 to 10 carbon atoms.

As a volatile silicone oil that can be used in the invention, mention may in particular be made of octamethylcyclotetrasiloxane, decamethylcyclopenta-siloxane, dodecamethylcyclohexasiloxane, heptamethyl-hexyltrisiloxane, heptamethyloctyltrisiloxane, hexa-methyldisiloxane, octamethyltrisiloxane, decamethyl-tetrasiloxane and dodecamethylpentasiloxane, and mixtures thereof.

The fluorinated volatile oil does not generally have a flashpoint.

As a fluorinated volatile oil, mention may be made of nonafluoroethoxybutane, nonafluoromethoxybutane, decafluoropentane, tetradecafluorohexane and dodecafluoro-pentane, and mixtures thereof.

The composition according to the invention comprises a volatile oil in any amount and preferably at a content ranging from 0.1% to 99% by weight relative to the total weight of the composition, more preferably from 2% to 80% by weight, and even more preferably ranging from 5% to 70% by weight.

The composition according to the invention can comprise at least one non-volatile oil.

The term "non-volatile oil" is intended to mean an oil that remains on the skin at ambient temperature and atmospheric pressure for at least several hours, and that has in particular a vapour pressure of less than 0.13 Pa (0.01 mm Hg).

These non-volatile oils may be hydrocarbon-based oils in particular of animal or plant origin, or silicone oils, or mixtures thereof. The term "hydrocarbon-based oil" is intended to mean an oil containing mainly hydrogen and carbon atoms, and optionally oxygen, nitrogen, sulphur and/or phosphorus atoms.

The non-volatile oils can in particular be chosen from hydrocarbon-based, where appropriate fluorinated, oils and/or non-volatile silicone oils.

As a non-volatile hydrocarbon-based oil, mention may in particular be made of:
  hydrocarbon-based oils of animal origin;
  hydrocarbon-based oils of plant origin, such as triglycerides consisting of fatty acid esters of glycerol, the fatty acids of which can have varied chain lengths of from $C_4$ to $C_{24}$, it being possible for the latter to be linear or branched, and saturated or unsaturated; these oils are in particular triglycerides of heptanoic acid or of octanoic acid, or alternatively wheatgerm, sunflower, grapeseed, sesame, maize, apricot, castor, shea, avocado, olive, soybean, sweet almond, palm, rapeseed, cottonseed, hazelnut, macadamia, jojoba, alfalfa, poppy, pumpkin seed, sesame, cucumber, blackcurrant seed, evening primrose, millet, barley, quinoa, rye, safflower, candlenut, passionflower or musk rose oil; shea butter; or triglycerides of caprylic/capric acids, such as those sold by the company Stéarineries Dubois or those sold under the names Miglyol 810®, 812 ® and 818® by the company Dynamit Nobel;
  synthetic ethers having from 10 to 40 carbon atoms;
  linear or branched hydrocarbons of mineral or synthetic origin, such as petroleum jelly, polydecenes, hydrogenated polyisobutene such as Parleam®, squalene, paraffin oils, and mixtures thereof;
  synthetic esters, such as oils of formula $R_1COOR_2$ in which $R_1$, represents the residue of a linear or branched fatty acid comprising from 1 to 40 carbon atoms and $R_2$ represents a hydrocarbon-based chain, in particular a branched hydrocarbon-based chain, comprising from 1 to 40 carbon atoms, provided that $R_1+R_2$ is $\geq 10$, such as, for example, Purcellin oil (cetearyl octanoate), isopropyl myristate, isopropyl palmitate, $C_{12}$ to $C_{15}$ alkyl benzoates, hexyl laurate, diisopropyl adipate, isononyl isononanoate, isodecyl neopentanoate, 2-ethyl-hexyl palmitate, isostearyl isostearate, 2-hexyldecyl laurate, 2-octyldecyl palmitate, 2-octyldodecyl myristate, heptanoates, octanoates, decanoates or ricinoleates of alcohols or of polyalcohols, such as propylene glycol dioctanoate; hydroxylated esters, such as isostearyl lactate, diisostearyl malate or 2-octyl-dodecyl lactate; esters of polyols and esters of pentaerythritol;
  fatty alcohols which are liquid at ambient temperature with a branched and/or unsaturated carbon chain having from 12 to 26 carbon atoms, such as octyldodecanol, isostearyl alcohol, oleyl alcohol, 2-hexyldecanol, 2-butyloctanol and 2-undecylpenta-decanol;
  higher fatty acids, such as oleic acid, linoleic acid, linolenic acid, and mixtures thereof.

The non-volatile silicone oils that can be used in the composition according to the invention can be non-volatile polydimethylsiloxanes (PDMSs), polydimethyl-siloxanes comprising pendant alkyl or alkoxy groups and/or alkyl or alkoxy groups at the end of the silicone chains, which groups each have from 2 to 24 carbon atoms, or phenylated silicones, such as phenyl trimethicones, phenyl dimethicones, phenyltrimethylsiloxydiphenylsiloxanes, diphenyl dimethicones or diphenylmethyldiphenyltrisiloxanes, and mixtures thereof.

The liquid fatty phase can be present in the composition according to the invention at a total content ranging from 0.5% to 98% by weight, relative to the total weight of the composition, preferably ranging from 2% to 50% by weight, preferably ranging from 5% to 40% by weight.

The fatty phase of the composition according to the invention can also comprise fatty substances other than the oils mentioned above, such as waxes or alternatively pasty fatty substances.

The term "waxes" is intended to mean fatty substances that are solid at ambient temperature.

The pasty fatty substances can be defined by means of at least one of the following physicochemical properties:
  a viscosity of 0.1 to 40 Pa.s (1 to 400 poises), measured at 40° C. using a Contraves TV rotary viscometer equipped with an MS-r3 or MS-r4 spindle at a frequency of 60 Hz,
  a melting point of 25-70° C., preferably 25-55° C.

As waxes that can be used according to the invention, mention may be made of:
  waxes of animal origin, such as beeswax, spermaceti, lanolin wax and lanolin derivatives, and plant waxes, such as carnauba wax, candelilla wax, ouricury wax, Japan wax, cocoa butter wax, cork fibre wax or sugarcane wax,
  mineral waxes, for example paraffin wax, petroleum jelly wax, lignite wax or microcrystalline waxes or ozokerites.
  synthetic waxes, among which polyethylene waxes, and waxes obtained by Fisher-Tropsch synthesis,
  silicone waxes, in particular substituted linear polysiloxanes; mention may, for example, be made of silicone polyether waxes, alkyl or alkoxy dimethicones having from 16 to 45 carbon atoms, and alkyl methicones, for instance the $C_{30}$-$C_{45}$ alkyl methicone sold under the trade name "AMS C 30" by Dow Corning,
  hydrogenated oils that are solid at 25° C., such as hydrogenated castor oil, hydrogenated jojoba oil, hydrogenated palm oil, hydrogenated tallow, hydrogenated coconut oil and fatty esters that are solid at 25° C., for instance the $C_{20}$-$C_{40}$ alkyl stearate sold under the trade name "Kester Wax K82H" by the company Koster Keunen,
  and/or mixtures thereof.

Polyethylene waxes, microcrystalline waxes, carnauba waxes, hydrogenated jojoba oil, candelilla waxes and beeswaxes, and/or mixtures thereof, will preferably be used.

Preferably, the waxes are present at a content ranging from 0.05% to 30% by weight, more preferably from 0.1% to 20%, relative to the total weight of the composition.

These fatty substances can in particular be chosen in a varied manner by those skilled in the art in order to prepare a composition having the desired properties, for example in terms of consistency or texture.

Hydrocarbon-based Block Copolymer

According to one embodiment of the invention, the composition may comprise, in addition to the resin, a hydrocarbon-based block copolymer, also called sequence copolymer, preferably a block copolymer that is soluble in the liquid fatty phase as defined above.

The copolymer can have at least one block whose glass transition temperature is preferably less than 20° C., preferably less than or equal to 0° C., preferably less than or equal to −20° C., more preferably less than or equal to −40° C. The glass transition temperature of said block can be between −150° C. and 20° C., in particular between −100° C. and 0° C.

In this case, when the resin has at least one glass transition temperature, the difference between the glass transition temperatures of the resin and of the copolymer is generally greater than 20° C., preferably greater than 40° C. and better still greater than 60° C.

When the resin has at least one glass transition temperature, the block copolymer is advantageously a plasticizer for the resin described above. The expression "plasticizer for the resin" is intended to mean a compound which, when combined in sufficient amount with the resin, decreases the glass transition temperature of the resin as defined above. The plasticizer compound decreases in particular the glass transition temperature of the polymer by at least 2, 3 or 4° C., preferably by 5° C. to 20° C. In a preferred embodiment, the plasticizer compound decreases in particular the glass transition temperature of the polymer by at least 2, 3 or 4° C., preferably by 5° C. to 20° C.

Block copolymers comprising at least one styrene block and at least one block comprising units chosen from butadiene, ethylene, propylene, butylene and isoprene, or a mixture thereof, are in particular preferred.

The hydrocarbon-based block copolymer can in particular be a diblock, triblock, multiblock, radial or star copolymer, or mixtures thereof.

Such hydrocarbon-based block copolymers are described in application US-A-2002/005562 and in patent U.S. Pat. No. 5,221,534.

According to a particularly preferred embodiment, the structuring agent of the oils is a lipophilic polymer.

The hydrocarbon-based block copolymer present in the composition according to the invention is an amorphous copolymer formed by polymerization of an olefin. The olefin can in particular be an elastomeric ethylenically unsaturated monomer.

As an example of an olefin, mention may be made of monomers of ethylenic carbide, having in particular one or two ethylenic unsaturations, having from 2 to 5 carbon atoms, such as ethylene, propylene, butadiene or isoprene.

Advantageously, the hydrocarbon-based block copolymer is an amorphous block copolymer of styrene and of olefin.

According to a preferred embodiment, the hydrocarbon-based block copolymer is hydrogenated so as to reduce the residual ethylenic unsaturations after polymerization of the monomers.

In particular, the hydrocarbon-based block copolymer is an optionally hydrogenated copolymer comprising styrene blocks and ethylene/$C_3$-$C_4$ alkylene blocks.

As a diblock copolymer which is preferably hydrogenated, mention may be made of styrene-ethylene/propylene copolymers, styrene-ethylene/butadiene copolymers, and styrene-ethylene/butylene copolymers. Diblock polymers are in particular sold under the name Kraton® G1701E by the company Kraton Polymers.

As a triblock copolymer, which is preferably hydrogenated, mention may be made of styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. Triblock polymers are in particular sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to a preferred embodiment of the invention, use may in particular be made of a mixture of a styrene-butylene/ethylene-styrene triblock copolymer and of a styrene-ethylene/butylene diblock copolymer, in particular those sold under the name Kraton® G1657M by the company Kraton Polymers.

Use may also be made of a mixture of styrene-butylene/ethylene-styrene hydrogenated triblock copolymer and of ethylene-propylene-styrene hydrogenated star polymer, such a mixture being in particular in isododecane. Such mixtures are, for example, sold by the company Penreco under the trade names Versagel® M5960 and Versagel® M5670.

A subject of the invention is also a skin make-up or care composition comprising a liquid fatty phase as defined above, comprising at least one resin having a number-average molecular weight of less than or equal to 10 000 g/mol, chosen from rosin, rosin derivatives, hydrocarbon-based resins, and mixtures thereof, as defined above, and at least one hydrocarbon-based block copolymer as defined above, the composition being able to form a deposit having a transfer index in the presence of sebum of less than or equal to 3.

According to a preferred embodiment, the composition according to the invention comprises a liquid fatty phase as defined above, a resin having a number-average molecular weight of less than or equal to 10 000 g/mol, chosen from rosin, rosin derivatives, hydrocarbon-based resins, and mixtures thereof, and at least one hydrocarbon-based block copolymer chosen from styrene-ethylene/propylene diblock copolymers, styrene-ethylene/butadiene diblock copolymers, styrene-ethylene/butadiene-styrene triblock copolymers, styrene-isoprene-styrene triblock copolymers and styrene-butadiene-styrene triblock copolymers, the weight ratio of the resin to the hydrocarbon-based block copolymer ranging from 1/1 to 4/1.

Preferably, the weight ratio of the resin to the hydrocarbon-based block copolymer ranges from 2.5/1 to 3.5/1.

According to a preferred embodiment, the resin is chosen from hydrogenated indene/methylstyrene/styrene copolymers.

The hydrocarbon-based block copolymer (or the mixture of hydrocarbon-based block copolymers) can be present at a content ranging from 0.1% to 10% by weight, relative to the total weight of the composition, preferably ranging from 0.5% to 5% by weight, and more preferably ranging from 1% to 3% by weight.

According to one embodiment, the hydrocarbon-based block copolymer is present in the composition according to the invention at a content such that the weight ratio of the resin to the hydrocarbon-based block copolymer ranges from 1/1 to 4/1.

According to a preferred embodiment, the weight ratio of the resin to the hydrocarbon-based block copolymer ranges from 2.5/1 to 3.5/1.

Thickening Agent for Other Oils:

The composition according to the invention can comprise, in addition to the hydrocarbon-based block copolymer, at least one oil-thickening agent, chosen from polymeric oil-thickening agents, mineral oil-thickening agents, and mixtures thereof.

The polymeric oil-thickening agent, present in the composition according to the invention, can be an amorphous polymer formed by polymerization of an olefin. The olefin can in particular be an elastomeric ethylenically unsaturated monomer. As an example of an olefin, mention may be made of monomers of ethylenic carbide, having in particular one or two ethylenic unsaturations, having from 2 to 5 carbon atoms, such as ethylene, propylene, butadiene or isoprene.

The polymeric oil-thickening agent is capable of thickening or of gelling the organic phase of the composition. The term "amorphous polymer" is intended to mean a polymer which has no crystalline form. The polymeric thickening agent can also be film-forming, i.e. it is capable of forming a film when it is applied to the skin.

The polymeric oil-thickening agent can in particular be chosen from:

polycondensates of polyamide type resulting from condensation between (α) at least one acid chosen from dicarboxylic acids containing at least 32 carbon atoms, such as fatty acid dimers, and (β) an alkylenediamine and in particular ethylenediamine, in which the polyamide polymer comprises at least one carboxylic acid end group esterified or amidated with at least one saturated and linear monoalcohol or one saturated and linear monoamine containing from 12 to 30 carbon atoms, and in particular ethylenediamine/stearyl dilinoleate copolymers such as the product sold under the name Uniclear 100 VG® by the company Arizona Chemical;

silicone polymers of the type:

1) of polyorganosiloxanes comprising at least two groups capable of establishing hydrogen interactions, these two groups being located in the polymer chain, and/or 2) of polyorganosiloxanes comprising at least two groups capable of establishing hydrogen interactions, these two groups being located on grafts or branches.

The groups capable of establishing hydrogen interactions can be chosen from ester, amide, sulphonamide, carbamate, thiocarbamate, urea, urethane, thiourea, oxamido, guanidino and biguanidino groups, and combinations thereof.

The silicone polymers used as structuring agents in the composition of the invention are polymers of the polyorganosiloxane type, such as, for example, those described in documents U.S. Pat. Nos. 5,874,069, 5,919,441, 6,051,216 and 5,981,680.

In particular, the silicone polymers are polyorgano-siloxanes as defined above and in which the units capable of establishing hydrogen interactions ae arranged in the polymer chain.

The silicone polymers can more particularly be polymers comprising at least one unit corresponding to general formula I:

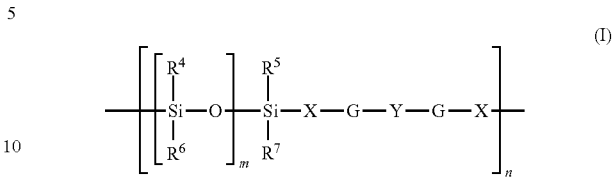

in which
1) $R^4$, $R^5$, $R^6$ and $R^7$ which may be identical or different, represent a group chosen from:
   saturated or unsaturated, linear, branched or cyclic $C_1$ to $C_{40}$ hydrocarbon-based groups which may contain, in their chain, one or more oxygen, sulphur and/or nitrogen atoms and which can be partially or totally substituted with fluorine atoms,
   $C_6$ to $C_{10}$ aryl groups optionally substituted with one or more $C_1$ to $C_4$ alkyl groups,
   polyorganosiloxane chains which may or may not contain one or more oxygen, sulphur and/or nitrogen atoms,
2) the X, which may be identical or different, represent a linear or branched $C_1$ to $C_{30}$ alkylene diyl group, which may contain, in its chain, one or more oxygen and/or nitrogen atoms,
3) Y is a $C_1$ to $C_{50}$ saturated or unsaturated, divalent linear or branched alkylene, arylene, cycloalkylene, alkylarylene or arylalkylene group, which can contain one or more oxygen, sulphur and/or nitrogen atoms, and/or can bear, as substituent, one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl groups and $C_1$ to $C_6$ aminoalkyl groups, or
4) Y represents a group corresponding to the formula:

in which
T represents a $C_3$ to $C_{24}$ saturated or unsaturated, linear or branched, trivalent or tetravalent hydrocarbon-based group optionally substituted with a polyorganosiloxane chain, and which can contain one or more atoms chosen from O, N and S, or T represents a trivalent atom chosen from N, P and Al, and
$R^8$ represents a linear or branched $C_1$ to $C_{50}$ alkyl group, or a polyorganosiloxane chain, which may contain one or more ester, amide, urethane, thiocarbamate, urea, thiourea and/or sulphonamide groups, which may or may not be linked to another chain of the polymer,
5) the G, which may be identical or different, represent divalent groups chosen from:

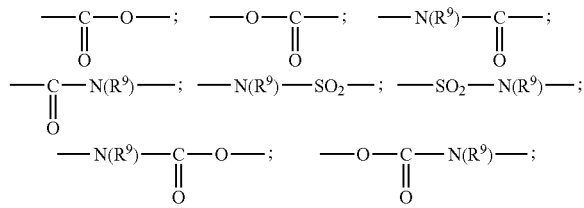

-continued

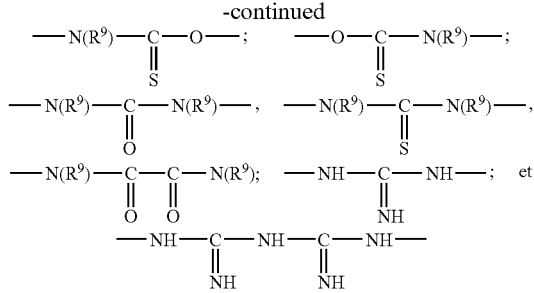

where $R^9$ represents a hydrogen atom or $C_1$ to $C_{20}$ linear or branched alkyl group, provided that at least 50% of the $R^9$ of the polymer represents a hydrogen atom and that at least two of the G groups of the polymer are a group other than:

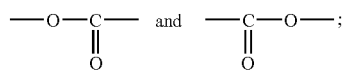

6) n is an integer ranging from 2 to 500, preferably from 2 to 200, and m is an integer ranging from 1 to 1000, preferably from 1 to 700, and even better still from 6 to 200.

According to the invention, 80% of the $R^4$, $R^5$, $R^6$ and $R^7$, of the polymer, are preferably chosen from methyl, ethyl, phenyl and 3,3,3-trifluoropropyl groups.

According to an advantageous embodiment, the groups capable of establishing hydrogen interactions are amide groups of formula —C(O)NH— and —NH—C(O)—.

In this case, the structuring agent can be a polymer comprising at least one unit of formula (III) or (IV):

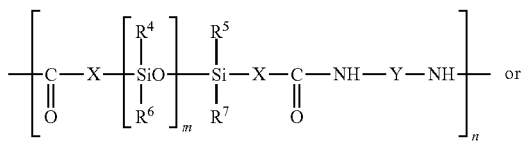

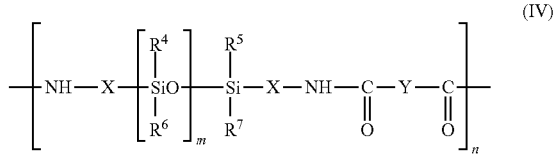

in which $R^4$, $R^5$, $R^6$, $R^7$, X, Y, m and n are as defined above.

In these polyamides of formula (III) or (IV), m ranges from 1 to 700, in particular from 15 to 500, and especially from 50 to 200, and n ranges in particular from 1 to 500, preferably from 1 to 100, and even better still from 4 to 25, X is preferably a linear or branched alkylene chain containing from 1 to 30 carbon atoms, in particular 1 to 20 carbon atoms, especially from 5 to 15 carbon atoms, and more particularly of 10 carbon atoms, and Y is preferably an alkylene chain which is linear or branched which can comprise rings and/or unsaturations, containing from 1 to 40 carbon atoms, in particular from 1 to 20 carbon atoms, and even better still from 2 to 6 carbon atoms, in particular of 6 carbon atoms, galactomanans containing from one to six, and in particular from two to four, hydroxyl groups per monosaccharide, substituted with a saturated or unsaturated alkyl chain, such as guar gum alkylated with $C_1$ to $C_6$, and in particular $C_1$ to $C_3$, alkyl chains, and mixtures thereof.

The composition according to the invention can also comprise at least one mineral oil-thickening agent, such as an organophilic clay or fumed silicas.

The organophilic clays are clays modified with chemical compounds that make the clay capable of swelling in oily media.

The clays are products that are already well known in themselves, and which are described, for example, in the work "Minéralogie des argiles [Mineralogy of clays], S. Caillère, S. Hénin, M. Rautureau, $2^{nd}$ edition 1982, Masson" the teaching of which is included herein by way of reference.

The clays are silicates containing a cation that can be chosen from calcium, magnesium, aluminium, sodium, potassium and lithium cations, and mixtures thereof.

By way of examples of such products, mention may be made of the clays of the smectite family, such as montmorillonites, hectorites, bentonites, beidellites or saponites, and of the family of vermiculites, stevensite and chlorites.

These clays may be of natural or synthetic origin. Preferably, clays which are cosmetically compatible and acceptable with keratin materials, such as the skin, are preferably used.

The organophilic clay can be chosen from montmorillonite, bentonite, hectorite, attapulgite and sepiolite, and mixtures thereof. The clay is preferably a bentonite or a hectorite.

These clays can be modified with a chemical compound chosen from quaternary amines, tertiary amines, amino acetates, imidazolines, aminated soaps, fatty sulphates, alkyl aryl sulphonates and amine oxides, and mixtures thereof.

As organophilic clays, mention may be made of quaternium-18 bentonites, such as those sold under the names Bentone 3, Bentone 38 and Bentone 38V by the company Rhéox, Tixogel VP by the company United Catalyst, and Claytone 34, Claytone 40 and Claytone XL by the company Southern Clay; stearalkonium bentonites, such as those sold under the names Bentone 27 by the company Rhéox, Tixogel LG by the company United Catalyst, and Claytone AF and Claytone APA by the company Southern Clay; quaternium-18/benzalkonium bentonite, such as those sold under the names Claytone HT and Claytone PS by the company Southern Clay.

The fumed silicas can be obtained by high-temperature hydrolysis of a volatile silicon compound in an oxhydric flame, producing a finely divided silica. This process makes it possible in particular to obtain hydrophilic silicas having a large number of silanol groups at their surface. Such hydrophilic silicas are, for example, sold under the names "Aerosil 130®", "Aerosil 200®", "Aerosil 255®", "Aerosil 300®" and "Aerosil 380®" by the company Degussa, and "Cab-O-Sil HS-5®", "Cab-O-Sil EH-5®", "Cab-O-Sil LM-130®", "Cab-O-Sil MS-55®" and "Cab-O-Sil M-5®" by the company Cabot.

It is possible to chemically modify the surface of said silica, by chemical reaction generating a decrease in the number of silanol groups. Silanol groups can in particular be substituted with hydrophobic groups: a hydrophobic silica is then obtained.

The hydrophobic groups may be:
trimethylsiloxyl groups, which are in particular obtained by treating fumed silica in the presence of hexamethyldisilazane. Silicas thus treated are called "Silica sylilate" according to the CTFA ($6^{th}$ edition, 1995). They are, for example, sold under the references "Aerosil R812®" by the company Degussa and "Cab-O-Sil TS-530®" by the company Cabot;
dimethylsilyloxyl or polydimethylsiloxane groups, which are in particular obtained by treatment of fumed silica in the presence of polydimethylsiloxane or of dimethyldichlorosilane. Silicas thus treated are called "silica dimethyl silylate" according to the CTFA (6$^{th}$ edition, 1995). They are, for example, sold under the references "Aerosil R972®" and "Aerosil R974®" by the company Degussa, and "Cab-O-Sil TS-610®" and "Cab-O-Sil TS-720®" by the company Cabot.

The fumed silica present preferably has a particle size that may be nanometric to micrometric, for example ranging from approximately 5 to 200 nm.

The mineral oil-thickening agent can be present in the composition according to the invention at a content ranging from 0.5% to 7% by weight, relative to the total weight of the composition, preferably at a content ranging from 1% to 5% by weight, and preferentially ranging from 1% to 3% by weight.

The oil-thickening agent is present in the composition according to the invention at a total content ranging from 0.1% to 20% by weight, relative to the total weight of the composition, preferably ranging from 0.5% to 15% by weight, and more preferentially ranging from 1% to 10% by weight.

Aqueous Phase

The composition according to the invention can comprise an aqueous phase.

The aqueous phase comprises water. The water can be a floral water such as cornflower water and/or a mineral water such as eau de Vittel, eau de Lucas or eau de La Roche Posay and/or a spring water.

The aqueous phase can also comprise organic solvents that are water-miscible (at ambient temperature –25° C.) such as, for example, monoalcohols containing from 2 to 6 carbon atoms, such as ethanol or isopropanol; polyols containing in particular from 2 to 20 carbon atoms, preferably containing from 2 to 10 carbon atoms, and preferentially containing from 2 to 6 carbon atoms, such as glycerol, propylene glycol, butylene glycol, pentylene glycol, hexylene glycol, dipropylene glycol or diethylene glycol;

glycol ethers (containing in particular from 3 to 16 carbon atoms), such as mono-, di- or tripropylene glycol ($C_1$-$C_4$) alkyl ethers, or mono-, di- or triethylene glycol ($C_1$-$C_4$)alkyl ethers, and mixtures thereof.

The aqueous phase can also comprise stabilizing agents, for example sodium chloride, magnesium dichloride and magnesium sulphate.

The aqueous phase can also comprise any water-soluble or water-dispersible compound compatible with an aqueous phase, such as gelling agents, film-forming polymers, thickeners or surfactants, and mixtures thereof.

Preferably, the aqueous phase may be present in the composition according to the invention at a content ranging from 1% to 95% by weight, relative to the total weight of the composition, and preferably from 3% to 80% by weight, and more preferably from 5% to 60% by weight.

Pulverulent Phase

The composition according to the invention can comprise a pulverulent phase, in particular chosen from pigments, fillers and/or pearlescent agents, and mixtures thereof.

According to a preferred embodiment, the composition according to the invention can comprise pigments.

The term "pigments" should be understood to mean mineral or organic particles that are insoluble in the liquid organic phase, and are intended to colour and/or opacify the composition.

The pigments can be mineral or organic pigments. As pigments, use may be made of metal oxides, such as iron oxides (in particular yellow, red, brown and black iron oxides), titanium dioxides, cerium oxide, zirconium oxide or chromium oxide; manganese violet, ultramarine blue, Prussian blue, cobalt blue, ferric blue, bismuth oxychloride, mother-of-pearl, mica coated with titanium or with bismuth oxychloride, coloured pearlescent pigments such as titanium mica with iron oxides, titanium mica with in particular ferric blue or chromium oxide, titanium mica with an organic pigment of the abovementioned type, and also pearlescent pigments based on bismuth oxychloride, and mixtures thereof.

Iron oxide or titanium dioxide pigments are preferably used.

The pigments may be treated with a hydrophobic agent to make them compatible with the organic phase of the composition. The hydrophobic-treatment agent may be chosen from silicones, such as methicones, dimethicones or perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, and amino acids; N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may, for example, be lysine, glutamic acid or alanine.

The term "alkyl" mentioned in the compounds mentioned above denotes in particular an alkyl group containing from 1 to 30 carbon atoms, preferably containing from 5 to 16 carbon atoms.

Hydrophobic-treated pigments are described in particular in application EP-A-1086683.

The pigments may be present in the composition according to the invention at a content of greater than or equal to 0.01% to 50% by weight, relative to the total weight of the composition, in particular ranging from 0.1% to 30% by weight, preferably ranging from 0.5% to 20% by weight, in particular ranging from 0.5% to 15% by weight.

Besides the pigments, the pulverulent phase of the composition according to the invention may comprise fillers and/or pearlescent agents.

According to a preferred embodiment, the composition according to the invention may comprise fillers.

The term "fillers" should be understood to mean colourless or white, mineral or synthetic particles of any shape, which are insoluble in the medium of the composition irrespective of the temperature at which the composition is manufactured.

The fillers may be mineral or organic and of any shape, platelet-shaped, spherical or oblong, irrespective of the crystallographic form (for example, lamellar, cubic, hexagonal, orthorhombic, etc.). Mention may be made of talc, mica, silica, kaolin, polyamide (Nylon®) powders, poly-β-alanine powders, polyethylene powders, poly(methyl methacrylate)s, polyurethane powders such as the powder of the copolymer of hexamethylene diisocyanate and of trimethylol hexyl lactone sold under the name Plastic Powder D-400 by the company Toshiki, tetrafluoroethylene polymer (Teflon®) powders, lauroyllysine, starch, boron nitride, polymeric hollow microspheres such as those of polyvinylidene chloride/acrylonitrile, for instance Expancel® (Nobel Industrie), or of acrylic acid copolymers, silicone resin powders, in particular silsesquioxane powders (silicone resin powders described in particular in patent EP 293795; Tospearls® from Toshiba, for example), elastomeric polyorganosiloxane particles, precipitated calcium carbonate, magnesium carbonate, magnesium hydrogen carbonate, hydroxyapatite, hollow silica microspheres, glass or ceramic microcapsules, and metal soaps derived from organic carboxylic acids containing from 8 to 22 carbon atoms, preferably from 12 to 18 carbon atoms, for example zinc stearate, magnesium stearate, lithium stearate, zinc laurate or magnesium myristate; barium sulphate, and mixtures thereof.

The fillers may be present in the composition according to the invention at a total content ranging from 0.01% to 99% by weight, relative to the total weight of the composition, preferably ranging from 0.02% to 9% by weight, and preferentially ranging from 0.05% to 90% by weight.

Besides the pigments and the fillers, the particulate phase of the composition according to the invention can comprise pearlescent agents.

The term "pearlescent agents" should be understood to mean iridescent particles, in particular produced by certain molluscs in their shell, or else synthesized, which are insoluble in the medium of the composition.

The pearlescent agents can be chosen from white pearlescent agents such as mica coated with titanium or with bismuth oxychloride, coloured pearlescent pigments such as titanium mica with iron oxides, titanium mica with in particular ferric blue or chromium oxide, titanium mica with an organic pigment of the abovementioned type, and also pearlescent agents based on bismuth oxychloride.

The pearlescent agents may be present in the composition according to the invention at a content ranging from 0.01% to 50% by weight, relative to the total weight of the composition, preferably ranging from 0.02% to 30% by weight, and preferentially ranging from 0.5% to 20% by weight.

Additional Dyes

The composition according to the invention can comprise additional dyes chosen from water-soluble and liposoluble dyes.

The water-soluble dyes are, for example, beetroot juice, methylene blue and caramel.

The term "liposoluble dyes" should be understood to mean compounds which are generally organic and are soluble in fatty substances such as oils.

The liposoluble dyes are, for example, Sudan red, D&C Red No. 17, D&C Green No. 6, β-carotene, soybean oil, Sudan brown, D&C Yellow No. 11, D&C Violet No. 2, D&C Orange No. 5, quinoline yellow, annatto and bromo acids.

The additional dyes may be present in the composition according to the invention at a content ranging from 0.001% to 30% by weight, relative to the total weight of the composition, preferably ranging from 0.01% to 20% by weight, and preferentially ranging from 0.02% to 10% by weight.

Additional Cosmetic Ingredients

The composition according to the invention may comprise at least one other cosmetic ingredient that may be chosen in particular from antioxidants, fragrances, preserving agents, neutralizing agents, surfactants, sunscreens, vitamins, moisturizers, self-tanning compounds, anti-wrinkle active agents, emollients, hydrophilic or lipophilic active agents, free-radical scavengers, deodorants, sequestering agents and film-forming agents, and mixtures thereof.

According to another aspect, a subject of the invention is also a process for making up and/or caring for the skin, consisting in applying to the skin a composition comprising a liquid fatty phase comprising a resin having a number-average molecular weight of less than or equal to 10 000 g/mol, chosen from rosin, rosin derivatives, hydrocarbon-based resins, and mixtures thereof, and at least one hydrocarbon-based block copolymer chosen from styrene-ethylene/propylene diblock copolymers, styrene-ethylene/butadiene diblock copolymers, styrene-ethylene/butadiene-styrene triblock copolymers, styrene-isoprene-styrene triblock copolymers and styrene-butadiene-styrene triblock copolymers, the weight ratio of the resin to the hydrocarbon-based block copolymer ranging from 1/1 to 4/1.

According to a preferred embodiment, the weight ratio of the resin to the hydrocarbon-based block copolymer of the composition of the make-up and/or care process ranges from 2.5/1 to 3.5/1.

According to a preferred embodiment, the resin of the composition of the make-up and/or care process is chosen from hydrogenated indene/methylstyrene/styrene copolymers.

Measurement of the Transfer Index

The transfer index in the presence of sebum, of the deposit obtained with the composition according to the invention, is determined according to the measuring protocol described hereinafter.

A support (square of 40 mm×40 mm) consisting of a layer of neoprene foam that is adhesive on one of its faces (sold under the name RE70X40 212B from the company Joint Technique Lyonnais Ind) is prepared. An adhesive crown having an internal diameter of 24 mm and a thickness of approximately 250 μm is attached to the non-adhesive face of the support. The composition is applied inside the crown and is levelled with a glass slide so as to obtain a deposit of the composition of approximately 250 μm thick, and then the crown is removed and the deposit is left to dry for 20 hours in an oven at 37° C.

The support is then bonded, by means of its adhesive face, to an endpiece with a diameter of 27 mm which is fixed on a press (Statif Manuel SV-1 from the company Imada Co Ltd) equipped with a dynanometer (DPS-5R from the company Imado Co Ltd).

On a piece of photo-quality coated paper (reference Epson S041061, 102 g/m²), a strip is drawn which is 4 cm wide and 21 cm long, and within this strip, 5 boxes each 4.2 cm long are drawn along the longitudinal axis of the strip. The paper is placed on the bed of the press.

In the centre of the first box, a drop of 10 μl of artificial sebum having the following composition is deposited:

| | |
|---|---|
| triolein | 29% |
| oleic acid | 28.5% |
| oleyl oleate | 18.5% |
| squalene | 14% |
| cholesterol | 7% |
| cholesteryl palmitate | 3% |

The support (comprising the sample of composition) is then pressed onto the first box of the paper strip, with a force of approximately 4 kg exerted for 5 seconds. The paper is then displaced in a regular, rectilinear fashion over the entire length of the strip, in such a way that the support is in contact with the entire length of the strip. The speed of displacement of the strip is of the order of 10 cm/s.

The trail of product deposited on the paper strip is then observed visually. A grade ranging from 0 to 5 in increments of 0.5 is awarded as a function of the number of boxes, from the first to the fifth, which have been traversed completely or partly by the possible trail of product.

For certain products, without coloration, a visualization step may be necessary in order to make the trail of product visible. By way of example, a compound capable of producing a coloured reaction on contact with the product transferred is used. According to another example, an active agent which emits in the visible range at least some of a UV radiation (Wood lamp) is incorporated into the product to be tested.

Grade 5 is awarded when, by observation, after the relative displacement between paper and support has taken place, there is substantially no product (less than 10%) remaining on the support. In this case, the transfer may be termed total.

Grade 5 is also awarded when the trail of product extends beyond the fifth box, independently of the amount of product remaining on the support.

Grade 0 is awarded when no product present on the support is transferred onto the paper strip. No visible trace can be observed on the sheet. The transfer may be termed zero.

By convention, the line of separation between box n and box n+1 forms part of box n.

The table below illustrates the way in which the other grades are awarded as a function of the point in boxes 1 to 5 at which the trail of product ends. For these grades, a larger or smaller amount of product remains on the support. The transfer is partial.

| No. of the box at which the trail of product stops | Grade | |
|---|---|---|
| | More than half of the box | Up to half of the box |
| 5 | 4.5 | |
| | | 4 |
| 4 | 3.5 | |
| | | 3 |
| 3 | 2.5 | |
| | | 2 |
| 2 | 1.5 | |
| | | 1 |
| 1 | 0.5 | |

The composition according to the invention can form a deposit having a transfer index in the presence of sebum of less than or equal 3, preferably less than or equal to 2, and more preferably less than or equal to 1.5.

The invention is presented in greater detail in the examples hereinafter.

EXAMPLES 1 to 7

7 foundations were prepared in the form of a water-in-oil emulsion having the following general formula:

| | | | % by mass |
|---|---|---|---|
| A1 | Polydimethylsiloxane alpha-omega oxyethylene/ oxypropylene in cyclopentasiloxane sold under the name Abil EM 97 by the company Goldschmidt | | 1.80 |
| | Isostearyl diglyceryl succinate | | 0.60 |
| | Isododecane | | W |
| | Cyclopentasiloxane | | 4.00 |
| A2 | Isododecane | | X |
| | Hydrogenated styrene/methylstyrene/indene copolymer sold under the reference Regalite R 1100 by the company Eastman Chemical | | Y |
| | Styrene-ethylene/butylene-styrene block copolymer sold under the reference Kraton G1657M by the company Kraton polymers | | Z |
| A3 | Cyclopentasiloxane | | 6.00 |
| | Iron oxides coated with aluminium stearoyl glutamate | | 2.1 |
| | Titanium dioxide coated with aluminium stearoyl glutamate | | 7.9 |
| A4 | Mixture of diphenyl dimethicone and of cyclopentasiloxane sold under the reference Mirasil C-DPDM by the company Rhodia | | 3.00 |
| A5 | Nylon 12 powder | | 8.00 |
| B | Demineralized water | | 41.40 |
| | Preserving agents | | 0.30 |
| | Magnesium sulphate | | 0.70 |
| | TOTAL | | 100% |

The content by mass of the hydrogenated styrene/methylstyrene/indene copolymer and of the styrene-ethylene/butylene-styrene block copolymer (Regalite R 1100+Kraton G1657M) in the composition is fixed at Y+Z=2.1%.

The content by mass of isodecane is constant in the composition, i.e. W+X=22.1%. A fraction of this isododecane is used to solubilize the two polymers.

The hydrogenated styrene/methylstyrene/indene copolymer/styrene-ethylene/butylene-styrene block copolymer (Regalite R 1100+Kraton G1657M) weight ratio is varied.

| | Example 1 | Example 2 | Example 3 | Example 4 | Example 5 | Example 6 | Example 7 |
|---|---|---|---|---|---|---|---|
| W (Isododecane A1) | 11.07 | 15.8 | 14.20 | 10.2 | 16.12 | 17.43 | 3.2 |
| X (Isododecane A2) | 11.03 | 6.3 | 7.90 | 11.9 | 5.98 | 4.67 | 18.9 |
| Y Regalite R 1100 | 2.1 | 1.68 | 1.60 | 1.4 | 1.3 | 1.08 | 1.05 |
| Z Kraton G1657M | 0 | 0.42 | 0.50 | 0.7 | 0.8 | 1.02 | 1.05 |
| % Regalite R 1100 | 100 | 80.00 | 76.19 | 66.67 | 61.90 | 51.43 | 50.00 |
| % Kraton G1657M | 0 | 20.00 | 23.81 | 33.33 | 38.10 | 48.57 | 50.00 |
| Ratio Regalite R1100/Kraton G1657M | | 4 | 3.2 | 2 | 1.62 | 1.06 | 1 |

2) Procedure
Phase Preparation:
   Preparation of A2: the Regalite R 1100 is dispersed in isododecane at 90° C., in a heating pan, and then the Kraton G1657M is added, and, once there is complete dispersion, the heating and the stirring are stopped.
   The pigments are ground in a three-roll mill (3 passages), in cyclopentasiloxane.
   The aqueous phase B is heated so as to disperse the preserving agent and the salt. It is then allowed to cool to ambient temperature.
Preparation Of The Emulsion:
   The constituents of phase A1 are weighed and are mixed with a Moritz stirrer at ambient temperature, and then A2, A3, A4 and A5 are added, taking care to homogenize well between each phase and to increase the stirring speed if necessary.
   The entire fatty phase A is then placed in a bath of cold water, still with stirring using a moritz stirrer, and B is gradually added, increasing the stirring speed if necessary.
   The mixture is left to stir for 10 min.
The transfer index in the presence of sebum of the compositions of Examples 1 to 7 is measured.
Results

|  | Example 1 | Example 2 | Example 3 | Example 4 | Example 5 | Example 6 | Example 7 |
|---|---|---|---|---|---|---|---|
| % Regalite R 1100 | 100 | 80.00 | 76.19 | 66.67 | 61.90 | 51.43 | 50.00 |
| % Kraton G1657M | 0 | 20.00 | 23.81 | 33.33 | 38.10 | 48.57 | 50.00 |
| Push & Pull 4 kg/dry | 1.25 | 0 | 0 | 0 | 0 | 0 | 0 |
| Push & Pull 4 kg/water | 1.25 | 0 | 0 | 0 | 0 | 0 | 0 |
| Push & Pull 4 kg/sweat | 1.5 | 0 | 0 | 0 | 0 | 0 | 0 |
| Push & Pull 4 kg/sebum | 2.5 | 3 | 0.5 | 1.5 | 1.25 | 1.5 | 1.5 |

Example 1 shows that the presence of the resin of hydrogenated styrene/methylstyrene/indene copolymer Regalite R 1100 makes it possible to obtain a deposit having a transfer index in the presence of sebum of less than 3.

Moreover, Examples 3 to 7 show that the transfer index is less than that of Example 1. The combination of hydrogenated styrene/methylstyrene/indene copolymer (the resin) and of styrene-ethylene/butylene-styrene block copolymer (the hydrocarbon-based block copolymer) therefore makes it possible to improve the non-transfer, the staying power, of the composition relative to a composition containing only the Regalite R 1100 resin.

When the hydrogenated styrene/methylstyrene/indene copolymer/styrene-ethylene/butylene-styrene block copolymer (Regalite R 1100/Kraton G1657M) weight ratio is between 1/1 and 3.5/1, the transfer index in the presence of sebum obtained is less than 2.

The best non-transfer result (lowest transfer index in the presence of sebum) is observed for a resin (Regalite R 1100)/(Kraton G1657M) weight ratio close to 3/1 (Example 3).

Moreover, the foundations of Examples 1 to 7, applied to the skin, make it possible to obtain a make-up exhibiting good staying power and good non-transfer.

The above written description of the invention provides a manner and process of making and using it such that any person skilled in this art is enabled to make and use the same, this enablement being provided in particular for the subject matter of the appended claims, which make up a part of the original description and including a skin make-up or care composition comprising a liquid fatty phase comprising at least one resin having a number-average molecular weight of less than or equal to 10 000 g/mol, chosen from rosin, rosin derivatives, hydrocarbon-based resins, and mixtures thereof, the composition being capable of forming a deposit having a transfer index in the presence of sebum of less than or equal to 3.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition, comprising a liquid fatty phase, comprising:
   at least one hydrogenated indene/methylstyrene/styrene copolymer resin having a number-average molecular weight of less than or equal to 10 000 g/mol; and
   at least one hydrocarbon-based block copolymer that is a mixture of a hydrogenated styrene-butylene/ethylene-styrene triblock copolymer and a styrene-ethylene/butylene diblock copolymer;
   wherein:
   a weight ratio of the hydrogenated indene/methylstyrene/styrene copolymer resin to the hydrocarbon-based block copolymer is from 1/1 to 3.5/1;
   the hydrocarbon-based block copolymer is present in an amount of from 0.1% to 10% by weight relative to a total weight of the composition; and
   the composition has a transfer index in the presence of sebum of less than or equal to 2.

2. The composition according to claim 1, wherein the composition has a transfer index in the presence of sebum of less than or equal to 1.5.

3. The composition according to claim 1, wherein the resin has a number-average molecular weight ranging from 250 to 10 000 g/mol.

4. The composition according to claim 1, wherein the resin has a number-average molecular weight of less than or equal to 5000 g/mol.

5. The composition according to claim 1, wherein the hydrogenated indene/methylstyrene/styrene copolymer resin is present in an amount of from 0.1% to 30% by weight based on a total weight of the composition.

6. The composition according to claim 1, wherein the liquid fatty phase further comprises at least one oil.

7. The composition according to claim 6, wherein the at least one oil is a volatile oil.

8. The composition according to claim 7, wherein the volatile oil is selected from the group consisting of hydrocarbon-based oils containing from 8 to 16 carbon atoms.

9. The composition according to claim 7, wherein the volatile oil is present in an amount of from 2% to 80% by weight, relative to a total weight of the composition.

10. The composition according to claim 1, wherein the liquid fatty phase is present in an amount of from 2% to 50% by weight relative to a total weight of the composition.

11. The composition according to claim 1, wherein the weight ratio of the at least one hydrogenated indene/methylstyrene/styrene copolymer resin to the hydrocarbon-based block copolymer is from 2.5/1 to 3.5/1.

12. The composition according to claim 1, further comprising at least one polymeric oil-thickening agent selected from the group consisting of:

polycondensates of polyamide type resulting from condensation between ($\alpha$) at least one acid chosen from dicarboxylic acids containing at least 32 carbon atoms, and ($\beta$) an alkylenediamine, in which the polyamide polymer comprises at least one carboxylic acid end group esterified or amidated with at least one saturated and linear monoalcohol or one saturated and linear monoamine containing from 12 to 30 carbon atoms;

silicone polymers:
1) of polyorganosiloxanes comprising at least two groups capable of establishing hydrogen interactions, these two groups being located in the polymer chain, and/or
2) of polyorganosiloxanes comprising at least two groups capable of establishing hydrogen interactions, these two groups being located on grafts or branches, the groups capable of establishing hydrogen interactions comprising at least one member selected from the group consisting of ester, amide, sulphonamide, carbamate, thiocarbamate, urea, urethane, thiourea, oxamido, guanidino and biguanidino groups.

13. The composition according to claim 1, further comprising at least one pulverulent phase comprising at least one of pigments and pearlescent agents.

14. The composition according to claim 1, further comprising an aqueous phase in an amount of from 3% to 80% by weight relative to a total weight of the composition.

15. The composition according to claim 1, further comprising at least one cosmetic ingredient selected from the group consisting of antioxidants, fragrances, preserving agents, neutralizing agents, surfactants, sunscreens, vitamins, moisturizers, self-tanning compounds, anti-wrinkle active agents, emollients, hydrophilic or lipophilic active agents, free-radical scavengers, sequestering agents, deodorants and film-forming agents.

16. A process for making up or caring for the skin, comprising applying the composition of claim 1 to the skin.

* * * * *